(12) United States Patent
Den Braber

(10) Patent No.: US 9,615,531 B2
(45) Date of Patent: Apr. 11, 2017

(54) PERONOSPORA RESISTANCE IN SPINACIA OLERACEA

(71) Applicant: RIJK ZWAAN ZAADTEELT EN ZAADHANDEL B.V., De Lier (NL)

(72) Inventor: Jan Hugo Den Braber, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 182 days.

(21) Appl. No.: 13/774,633

(22) Filed: Feb. 22, 2013

(65) Prior Publication Data

US 2013/0230635 A1 Sep. 5, 2013

Related U.S. Application Data

(63) Continuation-in-part of application No. PCT/EP2012/071299, filed on Oct. 26, 2012.

(30) Foreign Application Priority Data

Oct. 31, 2011 (EP) .................................... 11187288

(51) Int. Cl.
  *A01H 5/12* (2006.01)
  *A01H 1/04* (2006.01)
  *C12N 15/82* (2006.01)

(52) U.S. Cl.
  CPC ................. *A01H 5/12* (2013.01); *A01H 1/04* (2013.01); *C12N 15/8282* (2013.01)

(58) Field of Classification Search
  None
  See application file for complete search history.

(56) References Cited

U.S. PATENT DOCUMENTS

| | | | |
|---|---|---|---|
| 2009/0300786 A1* | 12/2009 | Baerends ................. | A01H 5/12 800/268 |
| 2009/0300788 A1* | 12/2009 | Baerends ................. | A01H 5/12 800/268 |
| 2010/0031385 A1 | 2/2010 | Baerends | |
| 2012/0054894 A1* | 3/2012 | Den Braber .................. | 800/260 |
| 2013/0055422 A1* | 2/2013 | Baerends ................. | A01H 5/12 800/260 |
| 2013/0055454 A1* | 2/2013 | den Braber .............. | A01H 5/12 800/260 |
| 2013/0230635 A1 | 9/2013 | den Braber et al. | |
| 2014/0065287 A1 | 3/2014 | den Braber et al. | |
| 2014/0068799 A1 | 3/2014 | den Braber et al. | |
| 2014/0068801 A1 | 3/2014 | den Braber et al. | |
| 2014/0068804 A1 | 3/2014 | den Braber et al. | |
| 2014/0068805 A1 | 3/2014 | den Braber et al. | |
| 2014/0068806 A1 | 3/2014 | den Braber et al. | |

OTHER PUBLICATIONS

Merriam-Webster_Definition of AS_2015.*
Feng et al., Plant Disease 98(1): 145-152 (2014).*
Correll et al., Eur J Plant Pathol 129:193-203 (2011).*
Irish et al., Plant Dis 91(11):1392-1396 (Nov. 2007).*
Correll et al., Eur J Plant Pathol 129:193-205 (2011).*
Irish et al., Phytopath 90(8):894-900 (2008).*
Proietti et al., Plant Physiol Biochem 47:717-23 (2009).*
Merriam-Webster, "as", accessed Sep. 27, 2016.*
Correll, J.C. et. al., "Spinach: better management of downy mildew and white rust through genomics", European Journal of Plant Pathology, vol. 129, No. 2, Feb. 2011, pp. 193-205.
Irish et. al. "Phytopathol." vol. 98, 2008, pp. 894-900.
"2011 APS-IPPC Joint Meeting Abstracts of Presentations" Phytopathology, 2011, 101(6):Supplemental, S1, S52.

* cited by examiner

*Primary Examiner* — David H Kruse
*Assistant Examiner* — Russell Boggs
(74) *Attorney, Agent, or Firm* — Vedder Price P.C.; Thomas J. Kowalski; Deborah L. Lu

(57) ABSTRACT

The present invention relates to a spinach plant which may comprise a single dominant gene which confers resistance to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410, wherein the gene is obtainable by introgression from a plant grown from seeds of which a representative sample was deposited with the NCIMB under NCIMB accession number 41857. The invention further relates to progeny of the plant, to propagation material therefore, such as seed, and to food products which may comprise the spinach leaves.

7 Claims, No Drawings

PERONOSPORA RESISTANCE IN SPINACIA OLERACEA

RELATED APPLICATIONS AND INCORPORATION BY REFERENCE

This application is a continuation-in-part application of international patent application Serial No. PCT/EP2012/071299 filed 26 Oct. 2012, which claims benefit of European patent application Serial No. 11187288.3 filed 31 Oct. 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The invention relates to a spinach plant which may comprise a single dominant gene which leads to resistance to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410. The invention also relates to progeny of said spinach plant, to propagation material of said spinach plant, to a cell of said spinach plant, to seed of said spinach plant, and to harvested leaves of said spinach plant. This invention further relates to use of a spinach plant in breeding to confer resistance against *Peronospora farinosa* f. sp. *spinaciae*.

BACKGROUND OF THE INVENTION

Spinach (*Spinacia oleracea*) is a flowering plant from the Amaranthaceae family that is grown as a vegetable. The consumable parts of spinach are the leaves from the vegetative stage. Spinach is sold loose, bunched, in pre-packed bags, canned, or frozen. There are three basic types of spinach, namely the savoy, semi-savoy and smooth types. Savoy has dark green, crinkly and curly leaves. Flat or smooth leaf spinach has broad, smooth leaves. Semi-savoy is a variety with slightly crinkled leaves. The main market for spinach is baby-leaf. Baby spinach leaves are usually of the flat-leaf variety and usually the harvested leaves are not longer than about eight centimeter. These tender, sweet leaves are sold loose rather than in bunches. They are often used in salads, but can also be lightly cooked.

Downy mildew—in spinach caused by the oomycete fungus *Peronospora farinosa* f. sp. *spinaciae* (formerly known as *P. effusa*)—is a major threat for spinach growers, because it affects the harvested plant parts, namely the leaves. Infection makes the leaves unsuitable for sale and consumption, as it manifests itself phenotypically as yellow lesions on the older leaves, and on the abaxial leaf surface a greyish fungal growth can be observed. The infection can spread very rapidly, and it can occur both in glasshouse cultivation and in soil cultivation. The optimal temperature for formation and germination of *P. farinosa* f. sp. *spinaciae* spores is 9 to 12° C., and it is facilitated by a high relative humidity. When spores are deposited on a humid leaf surface they can readily germinate and infect the leaf. Fungal growth is optimal between 8 and 20° C. and a relative humidity of ≥80%, and within 6 and 13 days after infection mycelium growth can be observed. Oospores of *P. farinosa* can survive in the soil for up to 3 years, or as mycelium in seeds or living plants.

In recent years various resistance genes have been identified that provide spinach plants with a resistance against downy mildew. However, it has been observed that previously resistant spinach cultivars can again become susceptible to the fungus. Investigations revealed that the cultivars themselves had not changed, and that the loss of downy mildew resistance must therefore be due to *P. farinosa* overcoming the resistance in these spinach cultivars. The downy mildew races (also called physios or isolates) that were able to infect resistant spinach cultivars were collected in a differential reference set, which can be used to test spinach cultivars for resistance. The differential set comprises a series of spinach cultivars (hybrids) that have different resistance patterns to the currently identified pathogenic races.

To date 14 pathogenic races of spinach downy mildew (Pfs) have been officially identified and characterized. Races 4 through 10 have been identified between 1990 and 2009 (Irish et al., 2008, *Phytopathol.* 98: 894-900), which illustrates the versatility and adaptability of the fungus to overcome resistances in spinach. In different geographical regions different combinations of pathogenic races occur, and the spinach industry therefore has a strong demand for spinach cultivars that are resistant to as many relevant downy mildew races as possible, preferably to all races that may occur in their region, and even to the newest threats that cannot be countered with the resistances that are present in the commercially available spinach cultivars.

In March and August 2011, the "International Working Group on *Peronospora farinosa*" (IWGP) designated two isolates as the type isolates for new races Pfs12 and Pfs13, respectively. As illustrated by Table 1, these newly identified *Peronospora* races can break the resistance of many spinach varieties that are currently used commercially worldwide, and they thus pose a serious threat to the productivity of the spinach industry.

Spinach variety Viroflay is susceptible to all known physios, while cultivars such as Lion and Lazio show resistance to multiple races. However, it is crucial to stay at the forefront of developments in this field, as *Peronospora* continuously develops the ability to break the resistances that are present in commercial spinach varieties. For this reason new resistance genes are very valuable assets, and they form an important research focus in spinach breeding. The goal of spinach breeders is to rapidly develop spinach varieties with a resistance to as many *Peronospora* races as possible, including the latest identified races, before these races become wide-spread and can threaten the industry.

Recently another new *Peronospora* isolate has been identified, termed UA4410, which subsequently has been officially named Pfs14. Along with the 13 other officially recognized Pfs races this isolate is publicly available from the Department of Plant Pathology, University of Arkansas, Fayetteville, Ark. 72701, USA, and also from NAK Tuinbouw, Sotaweg 22, 2371 GD Roelofarendsveen, the Netherlands.

No single dominant resistance gene is known that confers resistance to the new physios Pfs12, Pfs13 and UA4410. In the absence of a suitable resistance to counter this pathogenic threat, these new isolates may spread during the next growing seasons and cause great damage to the worldwide spinach industry in the immediate future.

In order to confer a resistance that is as broad as possible, i.e. that confers resistance to as many Pfs physios as possible, preferable to all known Pfs physios, it is very useful to be able to stack different resistance genes against *Peronospora* infection in spinach. Such a combination of different resistance genes on one gene segment is highly desirable. It is much easier if the resistance genes inherit as single dominant loci, because in that case the resistance pattern conferred by the dominant resistance gene cannot segregate away in the progeny of the cross, and will always inherit as one single set of resistances to various pathogenic races.

It is therefore the object of the invention to provide a single, dominant resistance gene in spinach, conferring resistance to various *Peronospora* races, including the ones that have been most recently identified, which enables the easy transfer of this broad resistance pattern to other spinach plants.

Citation or identification of any document in this application is not an admission that such document is available as prior art to the present invention.

SUMMARY OF THE INVENTION

The invention thus relates to spinach plants which may comprise a single dominant gene which confers resistance to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410, wherein the gene is obtainable by introgression from a plant grown from seeds of which a representative sample was deposited with the NCIMB under NCIMB accession number 41857.

The present invention relates to a new resistance gene—named R6—that confers resistance onto spinach plants to downy mildew races Pfs1, Pfs2, Pfs3, Pfs4, Pfs5, Pfs6, Pfs9, Pfs11, Pfs12, Pfs13 and UA4410. No spinach cultivars are known that have a resistance against the combination of these pathogenic races, that is conferred by a single dominant resistance gene. The current invention thus represents an important step forward in the field of downy mildew resistance in spinach. The new resistance gene of the invention (R6) behaves as a single dominant locus. It may be easily introduced into any other spinach plant, irrespective of the type (smooth, semi-savoy or savoy) or leaf morphology (smooth, weakly to strongly incised) or any other characteristic, to render it resistant against *Peronospora* isolates Pfs1, Pfs2, Pfs3, Pfs4, Pfs5, Pfs6, Pfs9, Pfs11, Pfs12, Pfs13 and UA4410.

Stacking of the R6 resistance gene of the invention that provides resistance to Pfs1, Pfs2, Pfs3, Pfs4, Pfs5, Pfs6, Pfs9, Pfs11, Pfs12, Pfs13 and UA4410 with other resistance genes known in the art and/or with those that will be identified in the future may lead to resistance against all known *Peronospora* races.

Spinach plants of the invention, carrying the new source of resistance designated as R6, may be crossed to other spinach plants carrying one or more resistance genes different from R6, to obtain an even broader resistance to the various *Peronospora* races.

The spinach plants of the invention are obtainable by crossing a first spinach plant with a second spinach plant, wherein one or both of the spinach plants may comprise the resistance gene of the invention, to obtain F1 plants.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DEPOSITS

The Deposits with the National Collections of Industrial, Marine and Food Bacteria (NCIMB) in Bucksburn, Aberdeen AB21 9YA, Scotland, UK, under deposit accession number 41857 were made pursuant to the terms of the Budapest Treaty. Upon issuance of a patent, all restrictions upon the deposit will be removed, and the deposit is intended to meet the requirements of 37 CFR §§1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The invention thus relates to a dominant resistance gene in spinach, that confers resistance to a broad range of pathogenic races, in particular the races Pfs1, Pfs2, Pfs3, Pfs4, Pfs5, Pfs6, Pfs9, Pfs11, Pfs12, Pfs13 and UA4410 of the fungus *Peronospora farinosa* f. sp. *spinaciae*. The resistance trait is genetically inherited as a single dominant locus. Its presence in a plant may be detected using a disease resistance assay as described in example 1. The disease resistance assay shows the phenotype, as illustrated by example 1. The genotype of the disease resistance may be assayed by testing the inheritance of the resistance gene. In an F2 population this gene segregates in a 3:1 ratio, i.e. on average 3 out of 4 F2 plants possess the resistance pattern of the invention, as is illustrated by example 2.

The single dominant R6 gene may be introduced into any other plant by introgression from a plant grown from seeds of which a representative sample was deposited with the NCIMB on Jul. 26, 2011 under NCIMB accession number 41857 or any other plant derived therefrom. The deposited seeds comprise the R6 gene and are thus a source of the gene. It may be introduced into other spinach plants of the same or a different type, such as savoy, semi-savoy and smooth as described in example 2. Spinach plants that carry the same dominant R6 gene as is found in plants grown from seeds deposited under NCIMB accession number 41857 but are not directly obtained therefrom are also plants of the invention.

The invention also relates to progeny of a spinach plant, which progeny is resistant to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410. Such progeny may be produced by sexual or vegetative reproduction of a plant of the invention or a progeny plant thereof. The progeny plant displays the R6 resistance trait in the same or in a similar way as the plant of which representative seed was deposited (NCIMB 41857). This means that such progeny has the same downy mildew resistance characteristics as claimed for the spinach plants of the invention.

As used herein the word "progeny" is intended to mean the offspring or the first and all further descendants from a cross with a plant of the invention that shows the R6 resistance trait. Progeny of the invention may comprise descendants of any cross with a plant of the invention that carries the R6 resistance trait. Such progeny is for example obtainable by crossing a first spinach plant with a second spinach plant, wherein one of the spinach plants was grown from seeds of a plant of the invention, representative seeds of which were deposited with the NCIMB under NCIMB accession number 41857, but may also be the progeny of any other spinach plant carrying the R6 gene as present in NCIMB 41857.

The said progeny plants comprise an introgression fragment that may comprise resistance gene R6, wherein the said introgression fragment is obtainable from a spinach plant of which representative seed is deposited with the NCIMB under NCIMB accession number 41857. The resistance trait thus has a genetic basis in the genome of a spinach plant, and using the assay described in example 1, spinach plants may be identified as being plants of the invention. It is understood that a parent plant that provides the trait of the invention is not necessarily a plant grown directly from the deposited seeds. The parent may also be a progeny plant from the seed, or a progeny plant from seeds that are identified to have (or to have acquired) the trait of the invention by other means. In one embodiment, the invention relates to spinach plants that carry the trait of the invention and that have acquired the said trait by introduction of the genetic information that is responsible for the trait from a suitable source, either by conventional breeding, or genetic modification, in particular by cis-genesis or trans-genesis. Cis-genesis is genetic modification of plants with a natural gene, encoding an (agricultural) trait from the crop plant itself or from a sexually compatible donor plant. Trans-genesis is genetic modification of a plant with a gene from a non-crossable species or with a synthetic gene.

In one embodiment, the source from which the genetic information is acquired is formed by plants grown from the deposited seeds, or by sexual or vegetative descendants therefrom. "Progeny" also encompasses plants that carry the trait of the invention which are obtained from other plants of the invention by vegetative propagation or multiplication.

The invention further relates to propagation material of a spinach plant of the invention, wherein a plant grown or regenerated from the said propagation material is resistant to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410. In one embodiment, the propagation material is suitable for sexual reproduction. Such propagation material may comprise for example microspores, pollen, ovaries, ovules, embryo sacs and egg cells. In another embodiment, the propagation material is suitable for vegetative reproduction. Such propagation material may comprise for example cuttings, roots, stems, cells, protoplasts, and tissue cultures of regenerable cells, parts of the plant that are suitable for preparing tissue cultures, in particular leaves, pollen, embryos, cotyledons, hypocotyls, meristematic cells, root tips, anthers, flowers, seeds and stems.

The invention further relates to a spinach plant grown or regenerated from the said propagation material of a plant of the invention, which plant is resistant to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410.

The invention further relates to a cell of a spinach plant of the invention, which cell may comprise a single dominant gene which leads to resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, wherein the said gene is as present in a spinach plant, representative seeds of which were deposited under NCIMB accession number 41857. The said cell thus may comprise the genetic information encoding the said resistance, in particular genetic information which is substantially identical, preferably completely identical to the genetic information encoding the said resistance trait of the spinach plant, representative seeds of which were deposited under NCIMB accession number 41857, more in particular the R6 gene described herein. Preferably, the cell of the invention is part of a plant or plant part, but the cell may also be in isolated form.

The invention also relates to a cell of a spinach plant of the invention, which cell may comprise a single dominant gene which leads to resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, and which plant is obtained by transferring the *Peronospora farinosa* f. sp. *spinaciae* resistance as found in seeds that were deposited under NCIMB accession number 41857 into an agronomically valuable spinach plant.

The invention further relates to seed of the spinach plant of the invention, which seed contain in their genome the genetic information that encodes the resistance trait of the invention.

The invention also relates to the use of seeds that were deposited under NCIMB accession number 41857 for transferring resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 into another agronomically valuable spinach plant.

The invention also relates to the use of a spinach plant of the invention that is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 due to the presence, in the genome of the plant, of the *Peronospora farinosa* f. sp. *spinaciae* resistance as found in seeds that were deposited under NCIMB accession number 41857 as a crop.

The invention further relates to the use of a spinach plant of the invention that is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 due to the presence, in the genome of the plant, of the *Peronospora farinosa* f. sp. *spinaciae* resistance as found in seeds that were deposited under NCIMB accession number 41857 as a source of seed.

The invention also relates to the use of a spinach plant of the invention that is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 due to the presence, in the genome of the plant, of the *Peronospora farinosa* f. sp. *spinaciae* resistance as found in seeds that were deposited under NCIMB accession number 41857 as a source of propagating material.

The invention also relates to the use of a spinach plant of the invention that is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 due to the presence, in the genome of the plant, of the *Peronospora farinosa* f. sp. *spinaciae* resistance as found in seeds that were deposited under NCIMB accession number 41857 for consumption.

The invention also relates to harvested leaves of spinach plants of the invention, to food products which may comprise harvested leaves of spinach plants of the invention, either in natural or in processed form, and to a container which may comprise one or more spinach plants of the invention in a growth substrate for harvest of leaves from the spinach plant in a domestic environment.

The invention further relates to the use of a spinach plant of the invention in breeding to confer resistance against *Peronospora farinosa* f. sp. *spinaciae*.

The invention also relates to the use of the *Peronospora farinosa* f. sp. *spinaciae* resistance as found in seeds that were deposited under NCIMB accession number 41857 for conferring resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 onto a *Spinacia oleracea* plant.

The invention further relates to the use of a *Spinacia oleracea* plant as a recipient of *Peronospora farinosa* f. sp. *spinaciae* resistance as found in seeds that were deposited under NCIMB accession number 41857.

In one aspect the invention relates to a method for production of a spinach plant which is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, which may comprise a) crossing a plant which may comprise a genetic determinant that leads to the said trait with another plant;
b) selecting plants that have the said trait in the F1;
c) optionally performing one or more rounds of selfing or crossing, and subsequently selecting, for a plant which may comprise/showing the trait of the invention.

The word “trait” in the context of this application refers to the phenotype of the plant. In particular, the word “trait” refers to the trait of the invention, more in particular to the resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410. The term “genetic determinant” is used for the genetic information in the genome of the plant that causes the trait of the invention. When a plant shows the trait of the invention, its genome may comprise the genetic determinant causing the trait of the invention. The plant thus has the genetic determinant of the invention.

It is clear that the parent that provides the trait of the invention is not necessarily a plant grown directly from the deposited seeds. The parent may also be a progeny plant from the seed or a progeny plant from seeds that are identified to have the trait of the invention by other means.

In one aspect, the invention relates to a method for production of a spinach plant which is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, which may comprise a) crossing a plant which may comprise the genetic determinant that leads to the said trait with another plant;
b) optionally backcrossing the resulting F1 with the preferred parent;
c) selecting for plants that have the said trait in the F1 or in the F2;
d) optionally performing one or more additional rounds of selfing or crossing, and subsequently selecting, for a plant which may comprise the said trait.

The invention additionally provides a method of introducing another desired trait into a spinach plant which is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, which may comprise:

a) crossing a spinach plant that is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, representative seed of which were deposited under deposit number NCIMB 41857, with a second spinach plant that may comprise a desired trait to produce F1 progeny;
b) selecting an F1 progeny that may comprise said resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 and the desired trait;
c) crossing the selected F1 progeny with either parent, to produce backcross progeny;
d) selecting backcross progeny which may comprise the desired trait and resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410; and
e) optionally repeating steps c) and d) one or more times in succession to produce selected fourth or higher backcross progeny that may comprise the desired trait and resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410. The invention includes a spinach plant produced by this method.

In one embodiment selection for plants that are resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 is done in the F1 or any further generation of a cross or alternatively of a backcross. Selection of plants may be done phenotypically as e.g. described in Example 1.

In one embodiment the plant which may comprise the genetic determinant is a plant of an inbred line, a hybrid, a doubled haploid, or of a segregating population.

The invention further provides a method for the production of a spinach plant resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 by using a doubled haploid generation technique to generate a doubled haploid line which may comprise the said trait.

The invention furthermore relates to hybrid seed that may be grown into a plant resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 and to a method for producing such hybrid seed which may comprise crossing a first parent plant with a second parent plant and harvesting the resultant hybrid seed, wherein said first parent plant and/or said second parent plant is the plant as claimed.

In one embodiment, the invention relates to a method for producing a hybrid spinach plant that is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, which may comprise crossing a first parent spinach plant with a second parent spinach plant and harvesting the resultant hybrid seed, of which the first parent plant and/or the second parent plant is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, and growing said hybrid seeds into hybrid plants that are resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410.

The invention also relates to a method for the production of a spinach plant that is resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 by using a seed that may comprise a genetic determinant in its genome that leads to resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 for growing the said spinach plant. The seeds are suitably seeds of which a representative sample was deposited with the NCIMB under deposit number NCIMB 41857.

The invention also relates to a method for seed production which may comprise growing spinach plants from seeds of which a representative sample was deposited with the NCIMB under deposit number NCIMB 41857, allowing the plants to produce seeds, and harvesting those seeds. Production of the seeds is suitably done by crossing or selfing.

In one embodiment, the invention relates to a method for the production of a spinach plant resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 by using tissue culture.

The invention furthermore relates to a method for the production of a spinach plant resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 by using vegetative reproduction.

In one embodiment, the invention relates to a method for the production of a spinach plant resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 by using a method for genetic modification to introgress the said trait into the spinach plant. Genetic modification may comprise transgenic modification or transgenesis, using a gene from a non-crossable species or a synthetic gene, and cisgenic modification or cisgenesis, using a natural gene, coding for an (agricultural) trait, from the crop plant itself or from a sexually compatible donor plant.

The invention also relates to a breeding method for the development of spinach plants that are resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 wherein germplasm which may comprise said trait is used. Representative seed of said plant which may comprise the genetic determinant and being representative for the germplasm was deposited with the NCIMB under deposit number NCIMB 41857.

In a further embodiment the invention relates to a method for the production of a spinach plant resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 wherein progeny or propagation material of a plant which may comprise the genetic determinant conferring said trait is used as a source to introgress the said trait into another spinach plant. Representative seed of said plant which may comprise the genetic determinant was deposited with the NCIMB under deposit number NCIMB 41857.

The invention provides preferably a spinach plant resistant to *Peronospora farinosa* f. sp. *spinaciae* races Pfs1, Pfs2, Pfs3, Pfs4, Pfs5, Pfs6, Pfs9, Pfs11, Pfs12, Pfs13, UA4410, which plant is obtainable by any of the methods herein described and/or familiar to the skilled person.

In the context of this application the resistance to *Peronospora farinosa* f. sp. *spinaciae* races Pfs1, Pfs2, Pfs3, Pfs4, Pfs5, Pfs6, Pfs9, Pfs11, Pfs12, Pfs13, UA4410 is preferably caused by a genetic determinant, in particular a single dominant gene, that is present in the genome of seed of deposit number NCIMB 41857.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Testing for the R6 Resistance Trait in Spinach Plants

The resistance to downy mildew infection was assayed as described by Irish et al. (2008; *Phytopathol.* 98: 894-900), using a differential set. Spinach plants of the invention (R6) were planted along with spinach plants from different other genotypes (see Table 1) in trays containing Scotts Redi-Earth medium, and fertilized twice a week after seedling emergence with Osmocote Peter's (13-13-13) fertilizer (Scotts). Plants were inoculated with a sporangial suspension ($2.5 \times 10^5$/ml) of a pathogenic race of *Peronospora farinosa* f. sp. *spinaciae* at the first true leaf stage. In this manner, 11 pathogenic races were tested (as shown in Table 1).

The inoculated plants were placed in a dew chamber at 18° C. with 100% relative humidity for a 24 h period, and then moved to a growth chamber at 18° C. with a 12 h photoperiod for 6 days. After 6 days, the plants were returned to the dew chamber for 24 h to induce sporulation, and they were scored for disease reaction.

Plants were scored as resistant or susceptible based on symptoms of chlorosis and signs of pathogen sporulation on the cotyledons and true leaves, as described by Irish et al. (2007; *Plant Dis.* 91: 1392-1396). Plants exhibiting any evidence of chlorosis and sporulation were considered susceptible. Resistant plants were re-inoculated to assess whether plants initially scored as resistant had escaped infection, or whether they were truly resistant.

Table 1 shows the differential set of spinach downy mildew races and the resistance of various spinach varieties (hybrids) to each one of these pathogenic races. A susceptible reaction is scored as "+" (indicating a successful infection by the fungus, with sporulation occurring on the entire cotyledon), and resistance is depicted as "−" (absence of sporulation on the cotyledons). A weak resistance response is indicated as "(+)", which in practice means a slightly reduced level of infection (with sporulation only occurring on the tips of the cotyledons in the differential seedling test). R6 is a line exhibiting the resistance of the present invention, and the resistance patterns of the parental lines of hybrid variety "Lion" are also shown.

Comparison of the parental lines of Lion to Lion itself reveals that the broad resistance pattern of Lion results from the combination of at least two resistance genes, coming from either of the parents, because both parents only possess parts of the resistance profile of the hybrid (Lion) that results from the crossing of these two lines. The genetic basis of the resistance in Lion is thus multigenic in nature, caused by the stacking of at least two resistance genes in the hybrid variety, and hence the genetic basis of the *Peronospora* resistance in Lion is entirely different from that in plants of the present invention.

In contrast, the R6 resistance trait of the present invention is conferred by a single dominant locus, which has the great advantage that the R6 resistance trait may be easily transferred to other spinach varieties by crossing/introgression, and that it may easily be combined with other resistance genes. When combined with selected other genes that e.g. confer resistance to downy mildew races Pfs7, Pfs8 and Pfs10, the R6 trait may be used to provide resistance to all downy mildew races known to date in spinach.

TABLE 1

| Race | Viro-flay | Resisto-flay | Califlay | Clermont | Campania | Boeing | Lion | Lazio | Whale | Polka | Pigeon | R6 | Lion male parent | Lion female parent |
|---|---|---|---|---|---|---|---|---|---|---|---|---|---|---|
| Pfs1 | + | − | − | − | − | − | − | − | − | − | − | − | − | − |
| Pfs2 | + | − | + | − | − | − | − | − | − | − | − | − | − | + |
| Pfs3 | + | + | − | − | − | − | − | − | − | − | − | − | − | − |
| Pfs4 | + | + | + | − | − | − | − | − | − | + | − | − | − | + |
| Pfs5 | + | + | − | + | − | − | − | − | − | − | − | − | − | − |
| Pfs6 | + | + | + | + | + | − | − | − | − | + | − | − | − | + |
| Pfs9 | + | + | − | + | + | − | − | − | − | − | − | − | − | − |
| Pfs11 | + | + | − | + | − | − | − | + | − | − | − | − | − | − |
| Pfs12 | + | + | − | + | + | + | − | + | − | − | − | − | + | − |
| Pfs13 | + | + | (+) | + | (+) | − | − | + | + | (+) | − | − | − | (+) |
| UA4410 | + | + | − | + | + | + | − | + | − | − | + | − | + | − |

Example 2

Introduction of the R6 Resistance Trait into Other Spinach Plants

A plant of the invention was crossed (as a father) with a plant that does not contain the R6 resistance trait, to obtain an F1. Thirty plants of the F1 population were tested for resistance to *Peronospora* race UA4410, as described in example 1. This particular resistance was absent from the mother plant used in the said cross. All 30 plants showed the resistance pattern of the invention, i.e. resistance to pathogenic race UA4410. This demonstrated that the R6 resistance gene inherits in a dominant manner.

In another experiment, a plant of the invention was crossed (as a mother) with a different spinach plant that does not contain the R6 resistance trait of the invention. Plants of the F1 population were selfed, and a total of 76 plants of the F2 generation were tested for *Peronospora* resistance, as described in example 1. As a positive discriminator for the presence of the R6 trait, resistance to Pfs11 was assayed, because this resistance was present in the mother plant (R6) but not in the father plant of the cross.

It was observed that Pfs11 resistance segregated in the F2 generation in a fashion that corresponds to dominant monogenic inheritance: 60 of the 76 F2 plants exhibited the R6-resistance pattern. Table 2 gives a detailed overview of the segregation of the R6 resistance trait in five F2 populations. Chi-square tests confirmed that the observed segregation in the F2 populations was consistent with a 3:1 segregation of the R6 resistance profile, as assayed here with resistance to Pfs11.

TABLE 2

| cross | | R6 trait present | R6 trait absent | Total | Chi square | >0.05 ? |
|---|---|---|---|---|---|---|
| 1 | observed | 8 | 3 | 11 | 0.862 | yes |
|   | expected (3:1) | 8.25 | 2.75 | 11 | | |
| 2 | observed | 14 | 3 | 17 | 0.484 | yes |
|   | expected (3:1) | 12.75 | 4.25 | 17 | | |
| 3 | observed | 11 | 3 | 14 | 0.758 | yes |
|   | expected (3:1) | 10.5 | 3.5 | 14 | | |
| 4 | observed | 7 | 2 | 9 | 0.847 | yes |
|   | expected (3:1) | 6.75 | 2.25 | 9 | | |
| 5 | observed | 20 | 5 | 25 | 0.564 | yes |
|   | expected (3:1) | 18.75 | 6.25 | 25 | | |

Table 2: segregation of the R6 resistance profile in five F2 populations from a cross between a spinach plant of the invention (mother) to a father plant of a different genotype, which lacket the R6 resistance trait. Chi-square tests confirm that the observed numbers of F2 plants that were resistant and sensitive were in agreement with what is expected if the trait segregates in a dominant monogenic fashion, namely 3:1 (resistant:sensitive). In all cases chi-square values are well above 0.05.

Similar segregation results were obtained when the progeny of a cross between a plant that carries the R6 resistance trait and a plant not carrying the said trait were assayed for the races Pfs1, Pfs2, Pfs3, Pfs4, Pfs5, Pfs6, Pfs9, Pfs11, Pfs12, Pfs13 and UA4410, which together constitute the R6 resistance profile.

The invention is further described by the following numbered paragraphs:

1. Spinach plant comprising a single dominant gene which confers resistance to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410, wherein the gene is obtainable by introgression from a plant grown from seeds of which a representative sample was deposited with the NCIMB under NCIMB accession number 41857.

2. Progeny of a spinach plant of paragraph 1, which progeny is resistant to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410, wherein the resistance is the result of the single dominant gene as defined in paragraph 1, which is as found in seeds of which a representative sample was deposited with the NCIMB under NCIMB accession number 41857.

3. Propagation material of a plant of paragraph 1 or 2, wherein a plant grown or regenerated from the material is resistant to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410.

4. Cell of a spinach plant of any one of paragraphs 1-3, which cell comprises a single dominant gene which leads to resistance to *Peronospora farinosa* f. sp. *spinaciae* races Pfs1, Pfs2, Pfs3, Pfs4, Pfs5, Pfs6, Pfs9, Pfs11, Pfs12, Pfs13 and UA4410, wherein the said gene is as present in a spinach plant, representative seeds of which were deposited under NCIMB accession number 41857.

5. Seed of a spinach plant of paragraph 1 or 2.

6. Harvested leaves of a spinach plant of any one of paragraphs 1-3.

7. Food product comprising the harvested leaves of paragraph 6.

8. Container comprising one or more spinach plants of any one of paragraphs 1-3 in a growth substrate for harvest of leaves from the spinach plant in a domestic environment.

9. Use of spinach plant of any of paragraphs 1-3, representative seeds of which were deposited under NCIMB accession number 41857, in breeding to confer resistance against *Peronospora farinosa* f. sp. *spinaciae*.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of producing a hybrid spinach seed comprising crossing a first parent spinach plant with a second parent spinach plant and harvesting the resultant hybrid spinach seed, wherein said first parent spinach plant comprises a R6 gene that confers resistance to a spinach plant to downy mildew races Pfs1, Pfs2, Pfs3, Pfs4, Pfs5, Pfs6, Pfs9, Pfs11, Pfs12, Pfs13 and UA4410 and that requires stacking with another downy mildew resistance gene for the spinach plant to have resistance to downy mildew races Pfs1, Pfs2, Pfs3, Pfs4, Pfs5, Pfs6, Pfs7, Pfs8, Pfs9, Pfs10, Pfs11, Pfs12, Pfs13 and UA4410, wherein the R6 gene is as found in a plant grown from seed deposited with the NCIMB under NCIMB accession number 41857.

2. The method of claim 1 wherein the second parent spinach plant comprises the R6 gene.

3. The method of claim 1 wherein the second parent spinach plant comprises another downy mildew resistance gene whereby a plant grown from the seed produced by the method has resistance to downy mildew races Pfs1, Pfs2, Pfs3, Pfs4, Pfs5, Pfs6, Pfs7, Pfs8, Pfs9, Pfs10, Pfs11, Pfs12, Pfs13 and UA4410.

4. A hybrid spinach seed, a plant grown from which having resistance to downy mildew races Pfs1, Pfs2, Pfs3, Pfs4, Pfs5, Pfs6, Pfs7, Pfs8, Pfs9, Pfs10, Pfs11, Pfs12, Pfs13 and UA4410 produced from the method of claim 3.

5. A hybrid spinach plant grown from the spinach seed of claim 4, having resistance to downy mildew races Pfs1, Pfs2, Pfs3, Pfs4, Pfs5, Pfs6, Pfs7, Pfs8, Pfs9, Pfs10, Pfs11, Pfs12, Pfs13 and UA4410.

6. A method of conferring resistance to a spinach plant not having resistance against *Peronospora farinosa* f. sp. *spinaciae* races Pfs1, Pfs2, Pfs3, Pfs4, Pfs5, Pfs6, Pfs9, Pfs11, Pfs12, Pfs13 and UA4410 comprising crossing a first parent spinach plant with a second parent spinach plant, wherein said first parent spinach plant comprises a R6 gene that confers resistance to the spinach plant to downy mildew races Pfs1, Pfs2, Pfs3, Pfs4, Pfs5, Pfs6, Pfs9, Pfs11, Pfs12, Pfs13 and UA4410 and that requires stacking with another downy mildew resistance gene for the spinach plant to have resistance to downy mildew races Pfs1, Pfs2, Pfs3, Pfs4, Pfs5, Pfs6, Pfs7, Pfs8, Pfs9, Pfs10, Pfs11, Pfs12, Pfs13 and UA4410, and said second parent spinach plant does not contain the R6 gene, wherein the R6 gene is as found in a plant grown from seed deposited with the NCIMB under NCIMB accession number 41857.

7. The method of claim 6 wherein the second parent spinach plant comprises another resistance gene whereby a plant grown from the seed produced by the method has resistance to downy mildew races Pfs1, Pfs2, Pfs3, Pfs4, Pfs5, Pfs6, Pfs7, Pfs8, Pfs9, Pfs10, Pfs11, Pfs12, Pfs13 and UA4410.

* * * * *